United States Patent
Shalev

(10) Patent No.: US 8,694,119 B2
(45) Date of Patent: Apr. 8, 2014

(54) ENDOVASCULAR ELECTROSTIMULATION NEAR A CAROTID BIFURCATION IN TREATING CEREBROVASCULAR CONDITIONS

(75) Inventor: Alon Shalev, Raanana (IL)

(73) Assignee: Samson NeuroSciences Ltd., Herzeliya Pituach (IL)

( * ) Notice: Subject to any disclaimer, the term of this patent is extended or adjusted under 35 U.S.C. 154(b) by 94 days.

(21) Appl. No.: 13/319,978

(22) PCT Filed: May 13, 2010

(86) PCT No.: PCT/IB2010/052134
§ 371 (c)(1),
(2), (4) Date: Nov. 17, 2011

(87) PCT Pub. No.: WO2010/131219
PCT Pub. Date: Nov. 18, 2010

(65) Prior Publication Data
US 2012/0059437 A1    Mar. 8, 2012

Related U.S. Application Data

(60) Provisional application No. 61/178,049, filed on May 14, 2009.

(51) Int. Cl.
*A61N 1/36* (2006.01)
(52) U.S. Cl.
USPC .............................................. 607/62; 607/50
(58) Field of Classification Search
None
See application file for complete search history.

(56) References Cited

U.S. PATENT DOCUMENTS

| 3,650,277 | A | | 3/1972 | Sjostrand et al. |
| 4,201,219 | A | | 5/1980 | Gonzalez |
| 4,791,931 | A | | 12/1988 | Slate |
| 5,199,428 | A | * | 4/1993 | Obel et al. ................. 607/44 |
| 5,669,924 | A | * | 9/1997 | Shaknovich ................ 623/1.11 |
| 5,727,558 | A | * | 3/1998 | Hakki et al. ................. 600/485 |
| 8,428,730 | B2 | * | 4/2013 | Stack et al. ................... 607/44 |
| 2004/0102818 | A1 | * | 5/2004 | Hakky et al. ................. 607/44 |
| 2005/0096710 | A1 | | 5/2005 | Kieval |
| 2006/0089678 | A1 | * | 4/2006 | Shalev ........................ 607/23 |
| 2007/0255379 | A1 | * | 11/2007 | Williams et al. ............. 607/120 |
| 2008/0177364 | A1 | * | 7/2008 | Bolea et al. ................. 607/117 |
| 2010/0023088 | A1 | * | 1/2010 | Stack et al. ................... 607/44 |
| 2010/0137949 | A1 | * | 6/2010 | Mazgalev et al. ............. 607/72 |
| 2010/0174347 | A1 | * | 7/2010 | Kieval et al. ................. 607/116 |
| 2010/0211131 | A1 | * | 8/2010 | Williams et al. .............. 607/44 |

FOREIGN PATENT DOCUMENTS

WO     2007092330 A1    8/2007

OTHER PUBLICATIONS

International Search Report dated Aug. 16, 2010 in corresponding International Application No. PCT/IB2010/052134.

* cited by examiner

*Primary Examiner* — Kennedy Schaetzle
(74) *Attorney, Agent, or Firm* — Dekel Patent Ltd.; David Klein

(57) ABSTRACT

An interventional system that utilizes a carotid chemoreceptor(s) and optionally baroreceptor(s) for inducing vasodilatation in blood vessels of the brain is provided for treating ischemic conditions of the CNS, such as ischemic stroke and cerebral vasospasm. The system includes an electrical signal generator and an endovascular module with electrode units for transiently being disposed in the internal and external carotid arteries, adjacent a carotid body.

8 Claims, 16 Drawing Sheets

ENDOVASCULAR ELECTROSTIMULATION NEAR A CAROTID BIFURCATION IN TREATING CEREBROVASCULAR CONDITIONS

FIELD OF THE INVENTION

This invention relates to a medical apparatus and a method for the treatment of brain vasospasm and ischemia. More particularly this invention relates to a system that uses a carotid baroreflex and chemoreflex in order induce vasodilatation in blood vessels of the brain.

BACKGROUND OF THE INVENTION

Cardiovascular Regulation of Blood Pressure

In human physiology, several negative feedback systems control blood pressure by adjusting heart rate, stroke volume, systemic vascular resistance and blood volume. Some allow rapid adjustment of blood pressure to cope with sudden changes such as the drop in cerebral blood pressure when rising up. Others act more slowly to provide long-term regulation of blood pressure. Even if blood pressure is steady, there may be a need to change the distribution of blood flow, which is accomplished mainly by altering the diameter of arterioles. Groups of neurons scattered within the medulla of the brain stem regulate heart rate, contractility of the ventricles, and blood vessel diameter. As a whole, this region is known as the cardiovascular center, which contains both a cardiostimulatory center and a cardioinhibitory center. The cardiovascular center includes a vasomotor center, which includes vasoconstriction and vasodilatation centers that influence blood vessel diameter. Since these clusters of neurons communicate with one another, function together, and are not clearly separated anatomically, they are usually taken as a group. The cardiovascular center receives input both from higher brain regions and from sensory receptors. Nerve impulses descend from higher brain regions including the cerebral cortex, limbic system and hypothalamus to affect the cardiovascular center. The two main types of sensory receptors that provide input to the cardiovascular center are baroreceptors and chemoreceptors. Baroreceptors are important pressure-sensitive sensory neurons that monitor stretching of the walls of blood vessels and the atria. Chemoreceptors monitor blood acidity, carbon dioxide level and oxygen level.

Output from the cardiovascular center flows along sympathetic and parasympathetic fibers of the autonomic nervous system. Sympathetic stimulation of the heart increases heart rate and contractility. Sympathetic impulses reach the heart via the cardiac accelerator nerves. Parasympathetic stimulation, conveyed along the vagus nerves, decreases heart rate. The cardiovascular center also continually sends impulses to smooth muscle in blood vessel walls via sympathetic fibers called vasomotor nerves. Thus autonomic control of the heart is the result of opposing sympathetic (stimulatory) and parasympathetic (inhibitory) influences. Autonomic control of blood vessels, on the other hand, is mediated exclusively by the sympathetic division of the autonomic nervous system.

In the smooth muscle of most small arteries and arterioles, sympathetic stimulation causes vasoconstriction and thus raises blood pressure. This is due to activation of alpha-adrenergic receptors for norepinephrine and epinephrine in the vascular smooth muscle. In skeletal muscle and the heart, the smooth muscle of blood vessels displays beta-adrenergic receptors instead, and sympathetic stimulation causes vasodilatation rather than vasoconstriction. In addition, some of the sympathetic fibers to blood vessels in skeletal muscle are cholinergic; they release acetylcholine, which causes vasodilatation.

Neural Regulation of Blood Pressure

Nerve cells capable of responding to changes in pressure or stretch are called baroreceptors. Baroreceptors in the walls of the arteries, veins, and right atrium monitor blood pressure and participate in several negative feedback systems that contribute to blood pressure control. The three most important baroreceptor negative feedback systems are the aortic reflex, carotid sinus reflex and right heart reflex.

A carotid sinus reflex is concerned with maintaining normal blood pressure in the brain and is initiated by baroreceptors in the wall of a carotid sinus. A carotid sinus is a small widening of the internal carotid artery just above the bifurcation of the common carotid artery. Any increase in blood pressure stretches the wall of the aorta and a carotid sinus, and the stretching stimulates the baroreceptors. A carotid sinus nerve, which is an afferent nerve tract that originates in carotid sinus baroreceptors, converges with the glossopharyngeal nerve, passes through the jugular foramen, reaches the rostral end of the medulla, and continues to the cardiovascular center. When an increase in aortic or carotid artery pressures is detected in this manner, the cardiovascular center responds via increased parasympathetic discharge in efferent motor fibers of the vagus nerves to the heart and by decreased sympathetic discharge in the cardiac accelerator nerves to the heart. The resulting decreases in heart rate and force of contraction lower cardiac output. In addition, the cardiovascular center sends out fewer sympathetic impulses along vasomotor fibers that normally cause vasoconstriction. The result is vasodilatation, which lowers systemic vascular resistance.

Carotid Sinus Baroreceptors

It has been demonstrated that there are two functionally different carotid sinus baroreceptors, where each type may play a different role in the regulation of blood pressure. Reference is now made to FIG. 2A, which is a plot of baroreceptor activity, measured on the ordinate as pulses or spikes per second against carotid sinus pressure on the abscissa, measured in mm Hg. Type I baroreceptors are characterized by a discontinuous hyperbolic transduction curve 10. Specifically, the electrical discharge pattern of these baroreceptors is such that, until a threshold carotid sinus pressure has been achieved, no signal is produced. However, when a carotid sinus pressure reaches the threshold, type I baroreceptor discharge commences abruptly, with an initial firing rate of about 30 spikes per second. Saturation occurs at about 200 mm Hg, at which the firing rate saturates at about 50 spikes per second. The nerve fibers connected to these types of baroreceptors are mostly thick, myelinated type A-fibers. Their conduction velocity is high, and they start firing at a relatively low threshold current (i.e., they have high impedance). The above characteristics for the type I baroreceptors suggest that they are involved in the dynamic regulation of arterial blood pressure, regulating abrupt, non-tonic changes in blood pressure.

Type II baroreceptors are pressure transducers that are characterized by a continuous transduction curve 12. Specifically, the electrical discharge pattern of these baroreceptors is such that they transmit impulses even at very low levels of arterial blood pressure. Consequently, there is no defined threshold for type II baroreceptors. The typical firing rate of type II baroreceptors in a normotensive individual is about five spikes per second. At a carotid sinus pressure of about 200 mm Hg, the firing rate saturates at about 15 spikes per second.

The nerve fibers connected to type II baroreceptors are either thin, myelinated type A fibers, or unmyelinated type C fibers. Their conduction velocity is low and, when stimulated experimentally, they start firing at a relatively high threshold current, due to their relatively low impedance. The above characteristics of type II baroreceptors suggest that they are involved in the tonic regulation of arterial blood pressure, and that they play a role in the establishment of baseline blood pressure (i.e., diastolic blood pressure).

Modulation of Baroreceptor Activity

The baroreceptive endings of a carotid sinus nerve and the aortic depressor nerve are the peripheral terminals of a group of sensory neurons with their soma located in the petrosal and nodose ganglia. The endings terminate primarily in the tunica adventitia of a carotid sinus and aortic arch. When stretched, they depolarize. Action potentials are consequently triggered from a spike-initiating zone on the axon near the terminal. The action potentials travel centrally to the nucleus tractus solitarius in the medulla. There, the sensory neurons synapse with a second group of central neurons, which in turn transmit impulses to a third group of efferent neurons that control the parasympathetic and sympathetic effectors of the cardiovascular system. The vascular structure of a carotid sinus and aortic arch determines the deformation and strain of the baroreceptor endings during changes in arterial pressure. For this reason, structural changes in the large arteries and decreased vascular distensibility, also known as compliance, are often considered the predominant mechanisms responsible for decreased baroreflex sensitivity and resetting of baroreceptors, which occur in hypertension, atherosclerosis, and aging.

The process of mechanoelectrical transduction in the baroreceptors depends on two components: (1) a mechanical component, which is determined by the viscoelastic characteristics of coupling elements between the vessel wall and the nerve endings, and (2) a functional component, which is related to (a) ionic factors resulting from activation of channels or pumps in the neuronal membrane of the baroreceptor region, which alter current flow and cause depolarization resulting in the generation of action potentials, and (b) paracrine factors released from tissues and cells in proximity to the nerve endings during physiological or pathological states. These cells include endothelial cells, vascular muscle cells, monocytes, macrophages, and platelets. The paracrine factors include prostacyclin, nitric oxide, oxygen radicals, endothelin, platelet-derived factors, and other yet unknown compounds. Extensive animal studies conducted in the 1990s support the concept that the mechanoelectrical transduction in baroreceptor neurons occurs through stretch-activated ionic channels, whose transduction properties are affected by the aforementioned factors.

There exists evidence indicating a dependency of the baroreflex on the temporal characteristics of discharges in the cardiovascular afferent fibers. The coupling of afferent baroreceptor activity with the central group of neurons leads to inhibition of sympathetic nerve activity. This coupling was examined by determining the relationship between afferent baroreceptor activity and efferent sympathetic nerve activity measured simultaneously.

Sustained inhibition of sympathetic nerve activity is not simply a function of baroreceptor spike frequency, but depends on the phasic burst pattern, with on and off periods during systole and diastole, respectively. Sympathetic nerve activity is disinhibited, because of what may be viewed as a "central adaptation," during nonpulsatile, nonphasic baroreceptor activity. It is not actually the pulse pressure that is important in sustaining sympathetic inhibition, but rather the magnitude of pulsatile distension of a carotid sinus and the corresponding phasic baroreceptor discharge. One would predict that a decrease in large artery compliance, as might occur in chronic hypertension or atherosclerosis, could result in a decrease in pulsatile distension of a carotid sinus and a blunting of the phasicity of baroreceptor input. There is progressive loss of the buffering capacity of the baroreflex because of central adaptation. It has been shown experimentally that the reflex inhibition of sympathetic nerve activity is most pronounced at lower frequencies of pulsatile pressure and during bursts of baroreceptor activity (between 1 and 2 Hz). When the burst or pulse frequency exceeded 3 Hz, there is known to be a significant disinhibition of sympathetic nerve activity, despite a maintained high level of total baroreceptor spike frequency per unit time. Thus, at very rapid pulse rates the efficiency of afferent-efferent coupling is reduced.

In a study conducted using young (1 year old) and old (10 years old) beagle dogs, it was found that the reflex inhibition of sympathetic nerve activity after a rise in carotid sinus pressure was maintained in the young but was very transient in the old dogs. The "escape" of sympathetic nerve activity from baroreflex inhibition occurred in the old dogs despite a maintained increase in afferent baroreceptor activity. Thus, the major defect in the baroreflex with aging may not be a structural vascular defect or an impaired baroreceptive process, but rather a central neural defect in the afferent-efferent coupling. It is proposed in U.S. Pat. No. 4,201,219 to employ a neurodetector device in order to generate pulsed electrical signals. The frequency of the impulses is utilized to pace the heart directly in order to modify the cardiac rate. This approach has not been generally accepted, as there were serious technical difficulties with the implantation, and the reliability of the apparatus. In U.S. Pat. No. 3,650,277 it is proposed to treat hypertension by stimulating afferent nerve paths from the baroreceptors of a patient, in particular the nerves from a carotid sinus. Short electrical pulses are used during a limited period of the cardiac cycle. It is necessary to synchronize an electrical signal generator to the heart activity of the patient, either by measuring electrical activity of the heart, or by using a transducer that is capable of measuring instantaneous blood pressure.

Another attempt at simulating the baroreceptor reflex is disclosed in U.S. Pat. No. 4,791,931, wherein a pressure transducer and a cardiac pacemaker are implanted. The pacing rate is variable and is responsive to arterial pressure.

Peripheral Chemoreceptors and Central Chemoreceptors

The primarily function of chemoreceptors is to regulate respiratory activity. This is an important mechanism for maintaining arterial blood $pO_2$, $pCO_2$, and pH within appropriate physiological ranges. For example, a fall in arterial $pO_2$ (hypoxemia) or an increase in arterial $pCO_2$ (hypercapnia) leads to an increase in the rate and depth of respiration through activation of the chemoreceptor reflex. Chemoreceptor activity, however, also affects cardiovascular function either directly (by interacting with medullary vasomotor centers) or indirectly (via altered pulmonary stretch receptor activity). Respiratory arrest and circulatory shock (these conditions decrease arterial $pO_2$ and pH, and increase arterial $pCO_2$) dramatically increase chemoreceptor activity leading to enhanced sympathetic outflow to the heart and vasculature via activation of the vasomotor center in the medulla. Cerebral ischemia activates central chemoreceptors, which produces simultaneous activation of sympathetic and vagal nerves to the cardiovascular system.

Carotid bodies are located on the external carotid arteries near their bifurcation with the internal carotids. Each carotid body is a few millimeters in size and has the distinction of having the highest blood flow per tissue weight of any organ in the body. Afferent nerve fibers join with the sinus nerve before entering the glossopharyngeal nerve. A decrease in carotid body blood flow results in cellular hypoxia, hypercapnia, and decreased pH that lead to an increase in receptor firing. The threshold pO2 for activation is about 80 mmHg (normal arterial pO2 is about 95 mmHg). Any elevation of pCO2 above a normal value of 40 mmHg, or a decrease in pH below 7.4 causes receptor firing. If respiratory activity is not allowed to change during chemoreceptor stimulation (thus removing the influence of lung mechanoreceptors), then chemoreceptor activation causes bradycardia and coronary vasodilation (both via vagal activation) and systemic vasoconstriction (via sympathetic activation). If respiratory activity increases, then sympathetic activity stimulates both the heart and vasculature to increase arterial pressure.

It is an object of the present invention to provide an improved method for treating cerebrovascular conditions, particularly ischemic events in the brain, by stimulating a carotid baroreceptor and/or chemoreceptor, thereby reducing carebrovascular tone, leading to increased cerebral blood flow (CBF) and potentially improved viability of metabolically compromised brain tissue.

It is another object of the invention to provide a simple-to-use endovascular system for electrically stimulating the nerves of carotid baroreceptors and/or chemoreceptors.

It is yet another object of the invention to provide a method to overcome tachyphylaxis of the CBF by alternating between stimulation of carotid chemoreceptor and carotid baroreceptor, and by alternating between baroreceptors and/or chemoreceptors on two sides of the body.

It is still other object of the invention to provide a method to reversibly and safely position (or anchor) an endovascular system for electrically engaging a carotid chemoreceptor and/or baroreceptor.

It is further an object of the invention to provide an improved method for treating ischemic events in the brain of a living body by estimating cerebral blood flow while stimulating either a carotid baroreceptor or carotid chemoreceptor, and adapting parameters of stimulation so as to optimize the response of the cerebral vascular bed to the stimulation

SUMMARY OF THE INVENTION

The invention provide a system for treating a cerebrovascular condition in a living body comprising: i) an implantable elongated electrostimulation module comprising a proximal end and a distal end, said distal end comprising a branching point at which said distal end is branched into at least a first and a second distal end members; (ii) at least one metallic electrode mounted to each of said first and second distal end members; (iii) an electromagnetic transceiver disposed at said proximal end; (iv) at least one conductive galvanically distinct wire extending through said module and connecting said transceiver with said electrodes; and (v) an electrical signal generator for producing an electrical waveform to be transmitted to said electrodes; said module being sized and shaped for transient endovascular positioning near to a carotid body of said living body, said branching point being adjacent to the bifurcation of said carotid, said at least first and second distal end members being inserted to internal and external carotid arteries, thereby enabling the stimulation by said electrodes of chemoreceptors and baroreceptors in said arteries adjacent to said bifurcation. Said module further comprises a generally tubular endovascular sheath, said sheath being disposed between said proximal end and said distal end, said sheath comprising one or more internal lumen, said lumen being adapted to house said conductive wire. The system of the invention preferably comprises means for estimating cerebral parameter selected from the group consisting of blood pressure, blood flow, blood velocity, and metabolic state of brain, said means being adjusted to generate a control signal indicative of said parameter, and wherein said electrical signal generator is capable of adapting said electrical waveform in accordance with said control signal so as to control said parameter. In a preferred embodiment of the invention, said parameter is blood flow and comprises the duration and intensity of vasodilation, and wherein said control signal comprises inducing a regimen of intermittently substantially normal and substantially increased blood flow, so as to prevent tolerance to said control signal. Said electrical waveform comprises a pulse train consisting of intermittently active and inactive periods, said active periods being characterized by a substantially non-zero electrical energy and said inactive period by zero electrical energy contained in said waveform. Said cerebrovascular condition is selected from the group consisting of cerebral hemorrhage, subarachnoid hemorrhage, cerebral vasospasm, brain ischemia, ischemic stroke, and traumatic brain injury. Said treating a cerebrovascular condition may comprise mitigating symptoms, or limiting damages resulting from ischemic state or trauma. Said distal end member is flexible and has a shape selected from the group consisting of serpentine, spiral, and helical. Said elongated module further comprises an endovascular anchoring member being capable of assuming (a) a collapsed state adapted to allow free longitudinal motion of said endovascular electrode inside a blood vessel lumen, and (b) a radially expanded state adapted to engage at least a longitudinal and an angular portion of said lumen, said endovascular anchoring member being reversibly transitioned between said collapsed state and radially expanded states.

The invention provides a method for treating a carebrovascular condition in a living body, comprising the following steps: (a) identifying a subject having a predetermined medical condition; (b) endovascularly placing elongated electrostimulation module adjacent to the carotid body of said subject, said module comprising a proximal end and a distal end, said distal end comprising a branching point at which said distal end is branched into at least a first and a second distal end members to which are mounted at least two metallic electrodes, said branching point being placed near to the bifurcation of said carotid, while inserting said at least first and second distal end members to the internal and external carotid arteries of the subject; (c) providing an electromagnetic transceiver disposed at said proximal end, at least one conductive galvanically distinct wire extending through said module and connecting said transceiver with said electrodes, and an electrical signal generator for producing an electrical waveform to be transmitted to said electrodes; (d) driving an electrical waveform from said generator to said carotid body via said at least to electrodes, so as to minimize distribution of electric current to anatomical locations other than carotid baroreceptor(s) or chemoreceptor(s). In a preferred aspect, the method of the invention further comprises performing measurement of a cerebrovascular parameter in said subject, and adjusting said electrical waveform accordingly, wherein said cerebrovascular parameter is selected from the group consisting of blood pressure, blood flow, blood velocity, and metabolic state of brain. Said condition to be treated is selected from the group consisting of cerebral hemorrhage, subarachnoid hemorrhage, cerebral vasospasm, brain ischemia, ischemic stroke, and traumatic brain injury. In one embodiment of the invention, driving an electrical waveform to said baroreceptor and said chemoreceptor occurs in a mutually exclusive manner, so that when said electrical waveform is driven to said baroreceptor, electrical waveform is not driven to said chemoreceptor, and vice versa, so as to reduce tachyphylaxis of each baroreceptor reflex and chemoreceptor reflex, while continuously maintaining cerebral vasodilatation. In other embodiment of the invention, driving an electrical waveform to said baroreceptor and said chemoreceptor occurs in a partially simultaneous manner, so that during a first phase of treatment, said electrical waveform is driven to both baroreceptor and chemoreceptor, during a second phase of treatment, said electrical waveform is driven only to baroreceptor, during a third phase of treatment, said electrical waveform is driven only to chemoreceptor, and during a fourth phase of treatment no electrical waveform is driven to either chemoreceptor or to baroreceptor, and wherein said first, second, third, and fourth phases of treatment are intermittently occurring. In one embodiment, one galvanically distinct electrode is endovascularly placed in a carotid sinus, and at least two galvanically distinct electrodes are endovascularly placed at either sides of a carotid bifurcation, adjacent a carotid body of said living body.

BRIEF DESCRIPTION OF THE DRAWINGS

For a better understanding of these and other objects of the present invention, reference is made to the detailed description of the invention, by way of example, which is to be read in conjunction with the following drawings of which detailed description is presented further below, wherein.

DETAILED DESCRIPTION OF THE INVENTION

Figure 1:
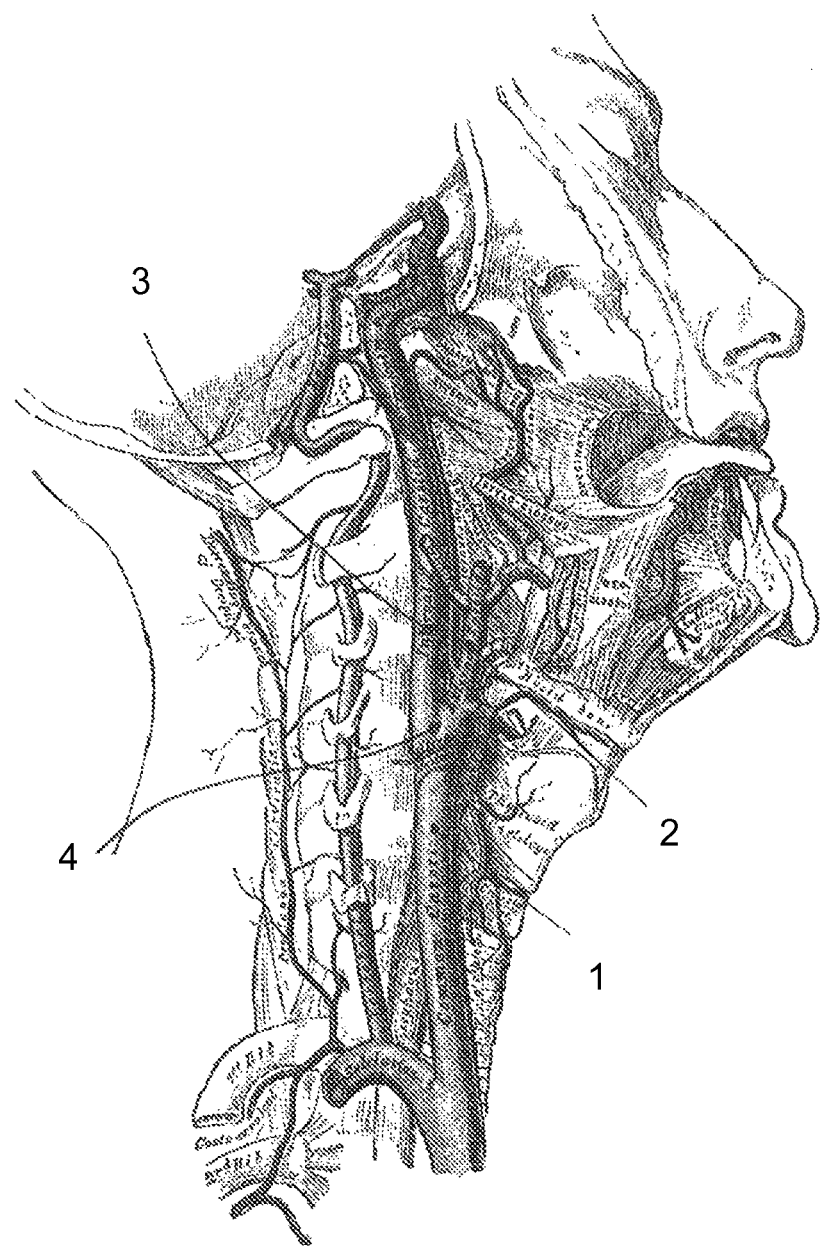
FIG. 1 is a general anatomic description, schematically depicting the major vascular structures of the right throat, neck and head, up to the temple region. Specifically, the figure depicts the common carotid artery (C.A.) that bifurcates into the internal carotid artery and the external carotid artery at the bifurcation.
Figure 2A:
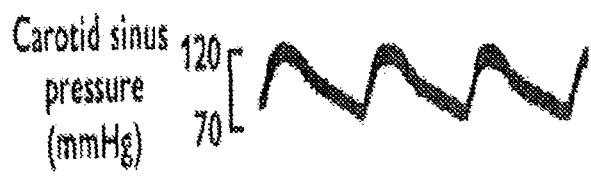
FIG. 2 depicts, in FIG. 2A-2F, electrical discharge patterns from baroreceptor and chemoreceptor fibers.
Figure 2E:
Figure 2B:
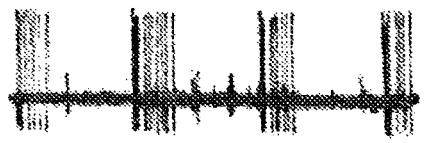
Figure 2F:
Figure 2C:
Figure 2D:

An efficient system for the stimulation of the nerves associated with carotid baroreceptors and chemoreceptors has now been suggested, aimed at inducing vasodilation in a brain of a living body. The system comprises a substantially longitudinal endovascular carotid body interface unit (EV-CBIU) and an electrical signal generator for producing an electrical waveform, said electrical signal generator being electrically coupled therewith, said EV-CBIU comprises a proximal user interface end, a distal electrode end (DEE) and two or more conductive leads disposed therebetween, said EV-CBIU is sized and shaped for transient endovascular positioning of said DEE adjacent a carotid body of said living body, said DEE bifurcates to two or more galvanically discrete stimulation electrodes. Said stimulation electrode comprises an elongate lead member and a conductive surface member, said conductive surface member being disposed externally thereto, said conductive surface member being galvanically connected to a corresponding said conductive lead. Preferably, said elongate lead member is galvanically isolated externally, and said stimulation electrode is characterized by a generally circular cross section. Said conductive surface member may comprise a generally cylindrical metal foil. Said metal may comprise, for example, a metal selected from stainless steel, platinum alloy, a platinum/iridium alloy, silver alloy, silver/silver chloride alloy, and nickel/titanium alloy. Said EV-CBIU preferably further comprises a generally tubular endovascular sheath, said sheath being disposed between said proximal user interface end and said DEE, said sheath comprising one or more internal lumens, said lumens being adapted to house said conductive leads, said lumens possibly being further divided into two or more sublumens, each sublumen being adapted to house said one or more conductive leads. Said sublumens may extend throughout the entire length of said sheath. The division in said divided lumen may be adjacent to said DEE, while further away from DEE it may be shaped as a unitary lumen. In one aspect, the system according to the invention may be adapted to allow longitudinal displacement of said conductive leads therein. In a preferred embodiment, the system according to the invention further comprises means for estimating important parameters characterizing the cerebrovascular system, also relevant from the diagnostic viewpoint, including blood flow, said means being capable of generating a control signal indicative of said blood flow, and wherein said electrical signal generator is capable of adapting said electrical waveform in accordance with said control signal whereby controlling said blood flow and its characteristics; said characteristics may comprise a desired duration of vasodilation, a desired intensity of vasodilation, etc. Said controlling may comprise, for example, a time-dependant control over a characteristic of said blood flow. Said time dependant control may comprise inducing a regimen of intermittently substantially normal and substantially increased blood flow, so as to prevent tolerance to said control signal.

Said means for estimating cerebral blood flow may comprise transcranial Doppler flowmeter, computerized tomography (CT) machine wherein said CT may comprise CT angiography (CTA), magnetic resonance imaging (MRI) machine, positron emission tomography (PET) machine, single photon emission computerized tomography (SPECT) machine, laser Doppler flowmeter, or Doppler enhanced ultrasound machine. The system according to the invention may comprise two EV-CBIU coupled to said electrical signal generator Said two EV-CBIU may be galvanically discrete, and said signal generator may be simultaneously driving an independent electrical waveform in each of said EV-CBIU.

In a system according to the invention, said electrical waveform usually comprises a pulse train. Said pulse may be a biphasic pulse. The pulse repetition rate may be between about 5 pulses per second to 30 pulses per second. In one embodiment of the invention, said pulse train comprised intermittently active and inactive periods, said active periods are characterized by a substantially non-zero electrical energy being contained in said waveform, said inactive period comprises a substantially zero electrical energy being contained in said waveform.

The invention is directed to an endovascular electrode mounted to an elongated member comprising a proximal end and a multiple channel distal end, said multiple channel distal end comprising at least a first and a second distal end members, wherein at least one metallic electrode is mounted to each of the said distal end members of the multiple channel distal end, and at least one galvanically distinct wire is extending through said elongated member and connected to each of the said metallic electrodes. Said elongated member is preferably flexible, and also said distal end member is preferably flexible. Said distal end member may have a shape selected from serpentine, spiral, and helical. Said metallic electrode may comprise a rigid body. Said elongated member may be cylindrically-shaped, and said distal end member may be cylindrically-shaped too. In one embodiment, said metallic electrode is cylindrically-shaped. Said endovascular electrode according to the invention may have an exterior surfaces conforming to an exterior surface of said distal end member, to form a medical probe with a substantially continuous exterior surface. Said endovascular electrode may have a cylindrical wall and a bore surrounded by a cylindrical wall. Said distal end member may be disposed within the bore of the corresponding metallic electrode.

The invention relates to a medical system comprising: one or more endovascular electrodes as described above, and an electrical signal generator for producing an electrical waveform being electrically coupled to at least two of said wires (conductive leads). Said elongated member may further comprise an endovascular anchoring member, said anchoring member being capable of assuming (a) a collapsed state adapted to allow free longitudinal motion of said endovascular electrode inside a blood vessel lumen, and (b) a radially expanded state adapted to engage at least a longitudinal and an angular portion of said lumen. Said endovascular anchoring member can be reversibly transitioned between said collapsed state and said radially expanded state, at a location adjacent said proximal end. Said endovascular anchoring member may be positioned on at least one of said distal end members. Said endovascular anchoring member may comprise a self-expanding structure. Said self-expanding structure may have the form of a cylindrical mesh. Said cylindrical mesh may comprise a radially smooth external contour, so as to minimize the risk of trauma to said blood vessel lumen, when said endovascular anchoring member is in its radially expanded state.

This invention thus provides a method for controlling a cerebrovascular function in a living body comprising the following steps: (a) identifying a subject having a predetermined medical condition; (b) endovascularly placing at least two galvanically distinct electrodes adjacent at least one carotid body of said subject; (c) Driving an electrical waveform to said carotid body via said at least to electrodes, so as to minimize distribution of electric current to anatomical locations other than said carotid baroreceptor. Said method according to the invention preferably further comprises the step of performing measurement of a cerebrovascular parameter in said body, and the step of adjusting said electrical waveform in accordance with the measurement and with the desired characteristics of the cerebrovascular parameters. Said cerebrovascular parameter may be blood pressure, blood flow, or blood velocity. Said cerebrovascular parameter may be a measure of the metabolic state of brain of said subject.

Said electrical waveform, provided by the generator which is a part of the system according to the invention, comprises pulses having stimulation rate above about 5 pulses per second and less than 15 pulses per second. Performing the measurement may comprise continuous measurement, periodic measurement, and intermittently continuous measurement. The medical conditions to affected, or treated, or mitigated comprises cerebral hemorrhage, subarachnoid hemorrhage, cerebral vasospasm, brain ischemia, ischemic stroke, or traumatic brain injury. In the method of the invention, the nerves to be stimulated comprise chemoreceptor, baroreceptors, or both. A method for controlling a carebrovascular function in a living body according to the invention comprises the following steps: (a) identifying a subject having a predetermined medical condition; (b) endovascularly placing at least two galvanically distinct electrodes adjacent at least one carotid baroreceptor and adjacent at least one carotid chemoreceptor of said subject; and (c) driving an electrical waveform to said baroreceptor and said chemoreceptor via said at least to electrodes, so as to minimize distribution of electric current to anatomical locations other than said carotid baroreceptor and chemoreceptor, respectively. The method may further comprise performing measurement of a cerebrovascular parameter in said body and adjusting a parameter of said electrical waveform in accordance with the value obtained by said measurement. Driving said electrical waveform to said baroreceptor and said chemoreceptor may occur simultaneously. Driving said electrical waveform to said baroreceptor and said chemoreceptor may occur in a mutually exclusive manner, so that when said electrical waveform is driven to said baroreceptor, electrical waveform is not driven to said chemoreceptor, and vice versa, so as to reduce tachyphylaxis of each baroreceptor reflex and chemoreceptor reflex, while continuously maintaining cerebral vasodilatation. Said driving the electrical waveform to said baroreceptor and said chemoreceptor may occur in a partially simultaneous manner, so that during a first phase of treatment, said electrical waveform is driven to both baroreceptor and chemoreceptor, during a second phase of treatment, said electrical waveform is driven only to baroreceptor, during a third phase of treatment, said electrical waveform is driven only to chemoreceptor, and during a fourth phase of treatment no electrical waveform is driven to either chemoreceptor or to baroreceptor, and wherein said first, second, third and fourth phases of treatment are intermittently occurring. The order of said first, second, third, and fourth phases may be predetermined according to a desired pattern, or it may be random. The sequential order of said first, second, third, and fourth phases relative to each other may be dynamically determined in accordance with the results of said measurement of cerebrovascular parameters. Said at least one galvanically distinct electrode is endovascularly placed in a proximal location of an internal carotid artery, and at least one galvanically distinct electrode is endovascularly placed in a proximal location of an external carotid artery on the same side of said living body. In other embodiments of the method according to the invention, at least one galvanically distinct electrode may be endovascularly placed in a carotid sinus, while at least one galvanically distinct electrode is endovascularly placed in an external carotid artery on the same side of said living body. In another embodiment, at least two galvanically distinct electrodes are endovascularly placed at either sides of a carotid bifurcation, adjacent to a carotid body of said living body. In a still another embodiment, at least one galvanically distinct electrode is endovascularly placed in a carotid sinus, and at least two galvanically distinct electrodes are endovascularly placed at either sides of a carotid bifurcation, adjacent to a carotid body of said living body. In another aspect of the invention, the method further comprises driving an electrical waveform to at least one additional baroreceptor or chemoreceptor on a contralateral side of said living body.

Thus, the invention relates to an implantable electrostimulation module comprising: (i) an elongated member comprising a proximal end and a multiple channel distal end, said multiple channel distal end comprising at least a first and a second distal end members; (ii) at least one metallic electrode mounted to each of the said distal end members of the multiple channel distal end; (iii) at least one galvanically distinct wire extending through said elongated member and connected to each of the said metallic electrode; and (iv) an electromagnetic transceiver disposed at said proximal end of elongated member and connected to each of said galvanically distinct wire; wherein said electromagnetic transceiver is adapted for extravascular implantation and wherein said elongated member and each of said metallic electrode are adapted for endovascular implantation. Said elongated member is preferably flexible, as well as said distal end member. Said distal end member may have a serpentine shape, spiral shape, or helical shape. In one embodiment, said metallic electrode may comprise a rigid body. Said elongated member may be cylindrically-shaped, as well as said distal end member, and also as said metallic electrode. The exterior surfaces of said metallic electrode may conform to an exterior surface of said distal end member to form a medical probe with a substantially continuous exterior surface. Said metallic electrode may have a cylindrical wall and a bore surrounded by a cylindrical wall. Said distal end member may be disposed within the bore of the corresponding metallic electrode. In one embodiment of the invention, an electrostimulation system is provided, comprising: (a) one or more implantable electrostimulation modules described above; and (b) an external electrical signal generator, capable of wirelessly energizing and controlling said electromagnetic transceiver to produce an electrical waveform at said metallic electrode. Said implantable electrostimulation module according to the invention, may comprise an elongated member which further comprises an endovascular anchoring member, said anchoring member being capable of assuming (a) a collapsed state adapted to allow free longitudinal motion of said implantable electrostimulation module inside a blood vessel lumen, and (b) a radially expanded state adapted to engage at least a longitudinal and an angular portion of said lumen. Said endovascular anchoring member can be reversibly transitioned between said collapsed state and radially expanded state, at a location adjacent said proximal end. Said endovascular anchoring member is preferably positioned on at least one of said distal end members. Said endovascular anchoring member may comprise a self-expanding structure, which may be in the form of a cylindrical mesh. Said cylindrical mesh may comprise a radially smooth external contour, so as to minimize the risk of trauma to said blood vessel lumen, when said endovascular anchoring member is in its radially expanded state. Said implantable electrostimulation module according to the invention may further comprise an outer pull-back sheath having a proximal end and a distal end, said sheath defining an elongated inner lumen being adapted for the endoluminal passage of said elongated member and each of said metallic electrode. Said elongated inner lumen may be adapted for the endoluminal passage of an electromagnetic transceiver. Said elongated inner lumen may comprise an elongated generally cylindrical inner lumen. In one embodiment, said first and second distal end members of the implantable electrostimulation module may assume a laterally oriented relaxed state and a parallel aligned compressed state. Said parallel aligned compressed state is assumed wherein each of said distal end members is generally contained within said outer pull-back sheath, and said laterally oriented relaxed state is assumed wherein each of said distal end members generally extends distally from said distal end of outer pull-back sheath. The implantable electrostimulation module may further comprise a distal spring, adapted to generate said laterally oriented relaxed stage. Said distal spring may be V-shaped, and it may be galvanically insulated from each of said metallic electrodes.

Said external electrical signal generator in the electrostimulation system according to the invention described above, namely in the system comprising (a) one or more implantable electrostimulation modules described above and (b) an external electrical signal generator capable of wirelessly energizing and controlling said electromagnetic transceiver to produce an electrical waveform at said metallic electrode, may be adapted to be wearable on a limb of a patient, in proximity with said implantable electromagnetic transceiver. Said external electrical signal generator may further comprise a user control interface. Each of the metallic electrodes in the system is adapted to be disposed in either of the common, the internal, and the external carotid artery, while being adjacent to a carotid bifurcation of a patient. Said electromagnetic transceiver is adapted to be disposed extravascularly in either a groin or upper leg of a patient.

To make the system of the invention still clearer, the major vascular structures of the right throat, neck and head, up to the temple region, are schematically depicted in FIG. 1. Specifically, the figure depicts the common carotid artery (1) that bifurcates into the internal carotid artery (3) and the external carotid artery (2), at a carotid bifurcation (4).

FIG. 2 depicts electrical discharge patterns from baroreceptor and chemoreceptor fibers; FIG. 2B depicts the discharge from a single baroreceptor fibre when the left carotid sinus is naturally perfused, as depicted in the pressure figure of FIG. 2A. FIG. 2D depicts the discharge from a single baroreceptor fibre when the left carotid sinus is artificially perfused, as depicted in the pressure figure of FIG. 2A. FIG. 2E depicts the discharge from a single chemoreceptor fibre when the left carotid sinus is perfused with arterial blood. FIG. 2F depicts the discharge from a single chemoreceptor fiber when the left carotid sinus is perfused with venous blood. Mean sinus pressure is 130 mmHg in both cases, and the respective average frequencies of discharge are 5 Hz and 18.5 Hz, respectively. The respective average frequencies of discharge were 33 impulse/s (2A and 2B) and 28 impulse/s (2C and 2D).

Figure 3:
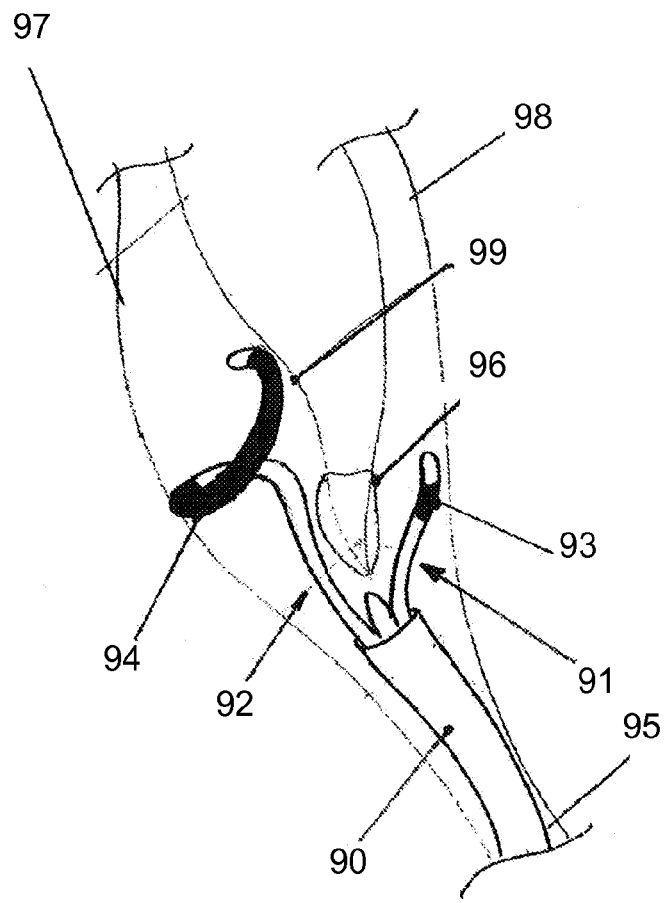
FIG. 3 to FIG. 7 are general anatomic descriptions schematically depicting selected embodiments of the present invention, showing an endovascularly positioned module branched to at least two members with at least two electrodes, the branching point of said module being adjacent to the bifurcation of the carotid, while the members are inserted to internal and external carotid arteries in which said electrodes stimulate the nerves of chemoreceptors and/or baroreceptors in said arteries adjacent to the bifurcation.

FIG. 3 schematically depicts a selected embodiment of the present invention. A multiple channel distal end (90) is endovascularly positioned near a carotid body (96). A first distal end member (91) is shown disposed within the external carotid artery (98). A second distal end member (92) is shown disposed within the internal carotid artery (97). One metallic electrode (93) is shown on the first distal end member (91). One metallic electrode (94) is shown on the second distal end member (92). In this particular embodiment of the present invention provides the first and second distal end members (91 and 92, respectively) are used to stimulate a carotid baroreceptor and a carotid chemoreceptor. The sinus is shown (99) and the common carotid artery (95).

Figure 4:
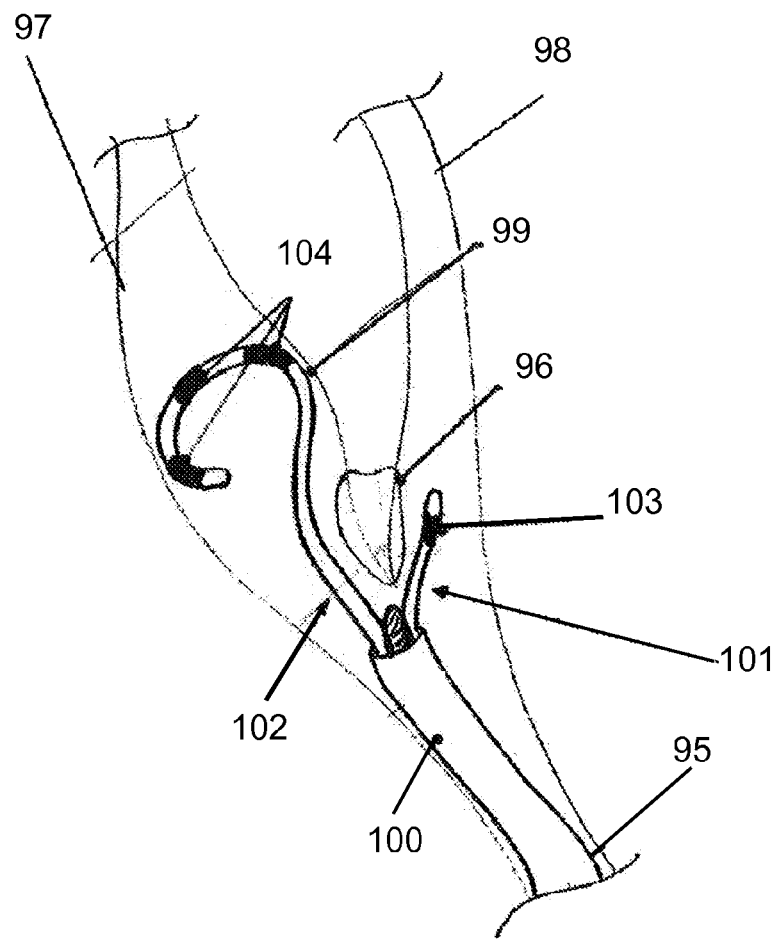
Figure 5:
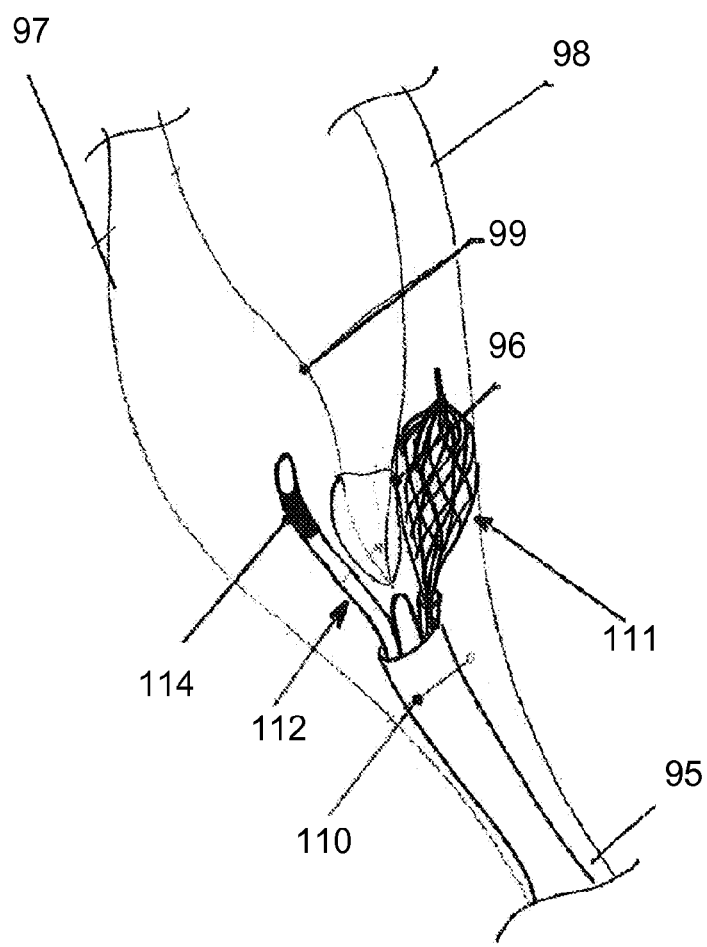

FIG. 4 schematically depicts a selected embodiment of the present invention. A multiple channel distal end (100) is endovascularly positioned near a carotid body (96). A first distal end member (101) is shown disposed within the external carotid artery (98). A second distal end member (102) is shown disposed within the internal carotid artery (97). One metallic electrode (103) is shown on the first distal end member (101). Three metallic electrodes (104) are shown on the second distal end member (102). In this particular embodiment of the present invention provides the first and second distal end members (101 and 102, respectively) are used to stimulate a carotid baroreceptor and a carotid chemoreceptor. FIG. 5 schematically depicts a selected embodiment of the present invention. A multiple channel distal end (110) is endovascularly positioned near a carotid body (96). A first distal end member (111) is shown disposed within the external carotid artery (98). A second distal end member (112) is shown disposed within the internal carotid artery (97). One metallic electrode (114) is shown on the second distal end member (92). In this particular embodiment, the first distal end member (111) serves as a metallic electrode and as an endovascular anchoring member that is in the form of a cylindrical mesh positioned on the first distal end member. In this particular embodiment of the present invention provides the first and second distal end members (111 and 112, respectively) are used to stimulate a carotid baroreceptor and a carotid chemoreceptor.

Figure 6:
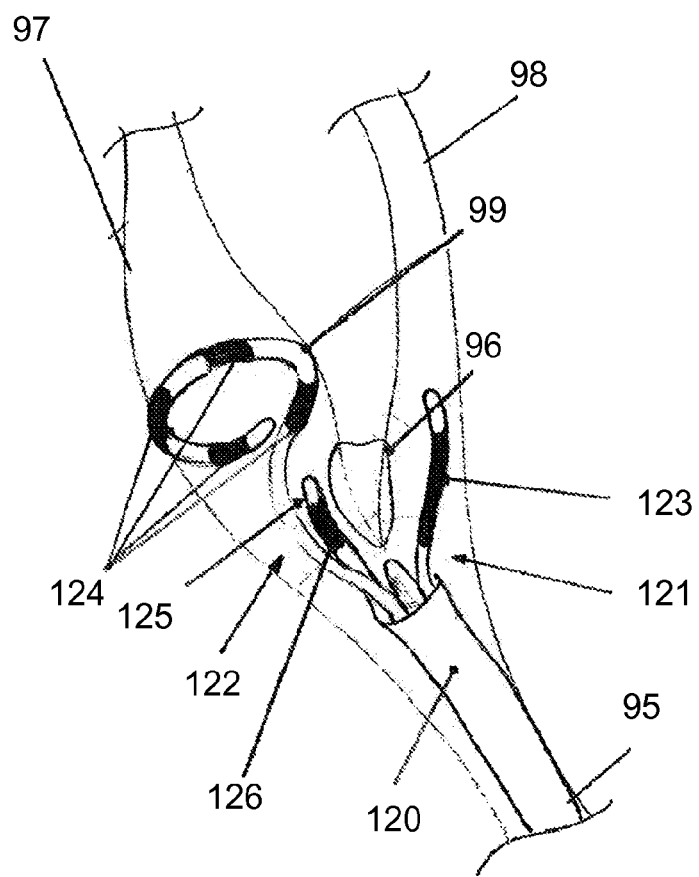

FIG. 6 schematically depicts a selected embodiment of the present invention. A multiple channel distal end (120) is endovascularly positioned near a carotid body (96). A first distal end member (121) is shown disposed within the external carotid artery (98). A second distal end member (122) is shown disposed within the internal carotid artery (97). A third distal end member (125) is shown disposed within the internal carotid artery. One metallic electrode (123) is shown on the first distal end member (121). Four metallic electrodes (124) are shown on the second distal end member (102). One metallic electrode (126) is shown on the third distal end member (125). In this particular embodiment of the present invention provides, the first and second distal end members (121 and 122, respectively) are used to stimulate a carotid baroreceptor and the first and third distal end members (121 and 125, respectively) are used to stimulate a carotid chemoreceptor.

Figure 7:
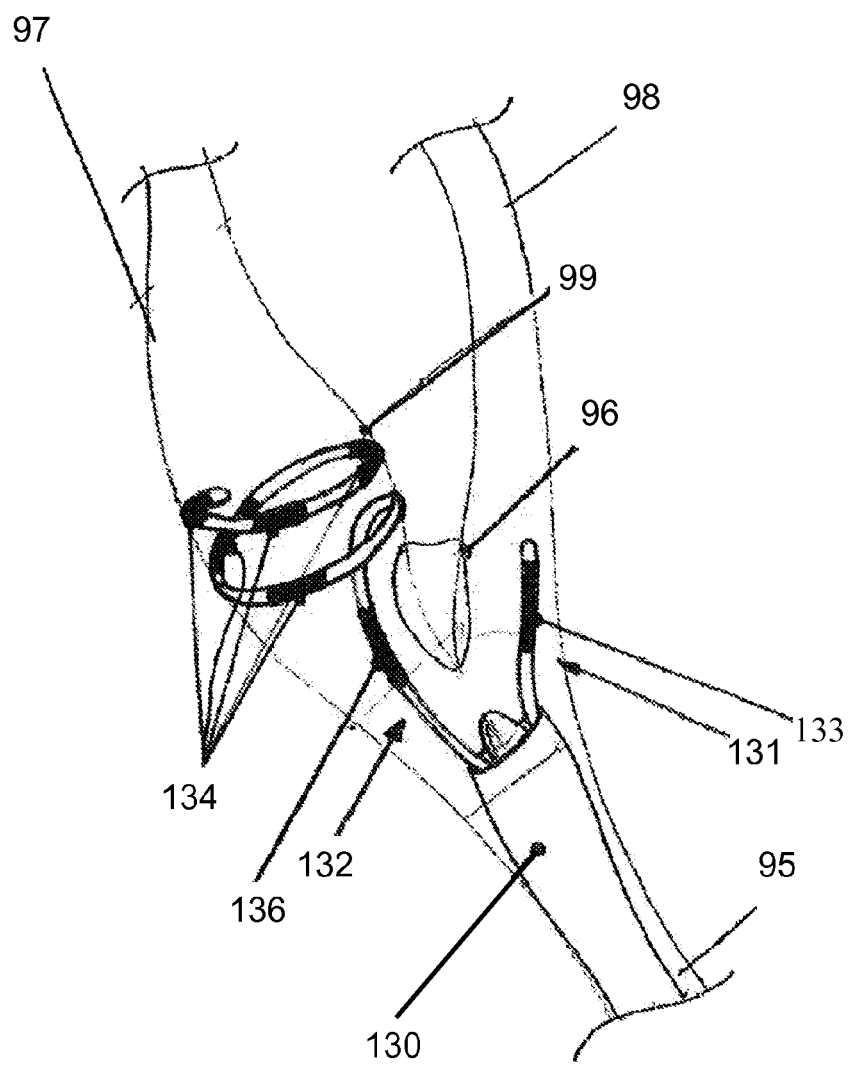

FIG. 7 schematically depicts a selected embodiment of the present invention. A multiple channel distal end (130) is endovascularly positioned near a carotid body (96). A first distal end member (131) is shown disposed within the external carotid artery (98). A second distal end member (132) is shown disposed within the internal carotid artery (97). One metallic electrode (133) is shown on the first distal end member (131). Five metallic electrodes are schematically depicted on the second distal end member (102), of which four metallic electrodes (134) are disposed on the distal end of the second distal end member (132) and one metallic electrode (136) is disposed on the proximal end of the second distal end member (132). In this particular embodiment of the present invention provides, the first distal end member (131) in conjunction with the four distal metallic electrodes (134) that are mounted to the second distal end member (132) are used to stimulate a carotid baroreceptor, while the first distal end member (131) in conjunction with the proximal metallic electrode (136) that is mounted to the second distal end member (132) are used to stimulate a carotid chemoreceptor.

Figure 8:
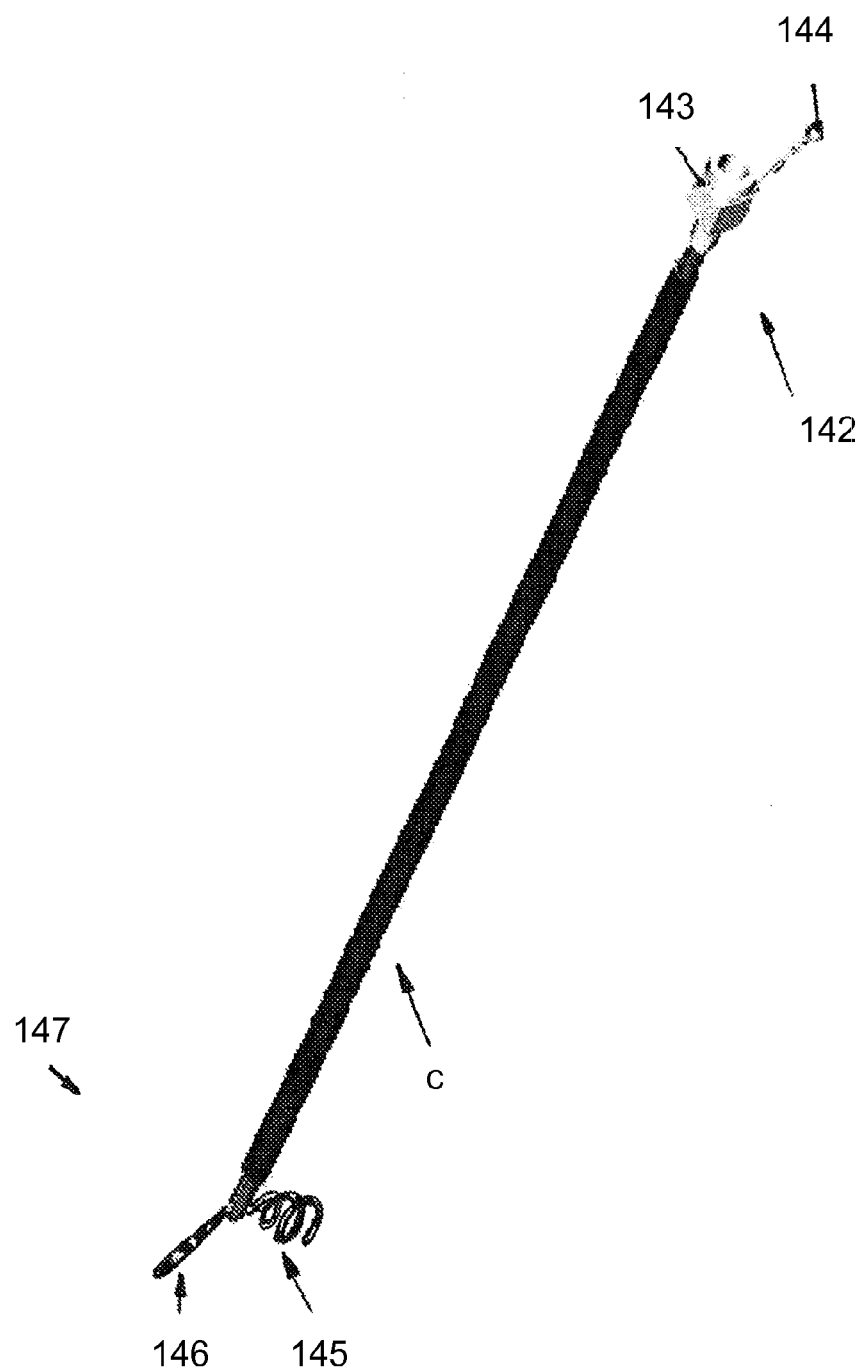
FIG. 8 schematically depicts a catheter which is an embodiment of an electrostimulation module according to the invention adapted for endovascular implantation.

FIG. 8 schematically depicts the endovascular carotid body interface unit (EV-CBIU) (140) in a selected embodiment of the present invention. A standard endovascular angiography port (143) and an electrical connector (144) are both depicted as part of the proximal user interface end (142) of the EV-CBIU.

Figure 9:
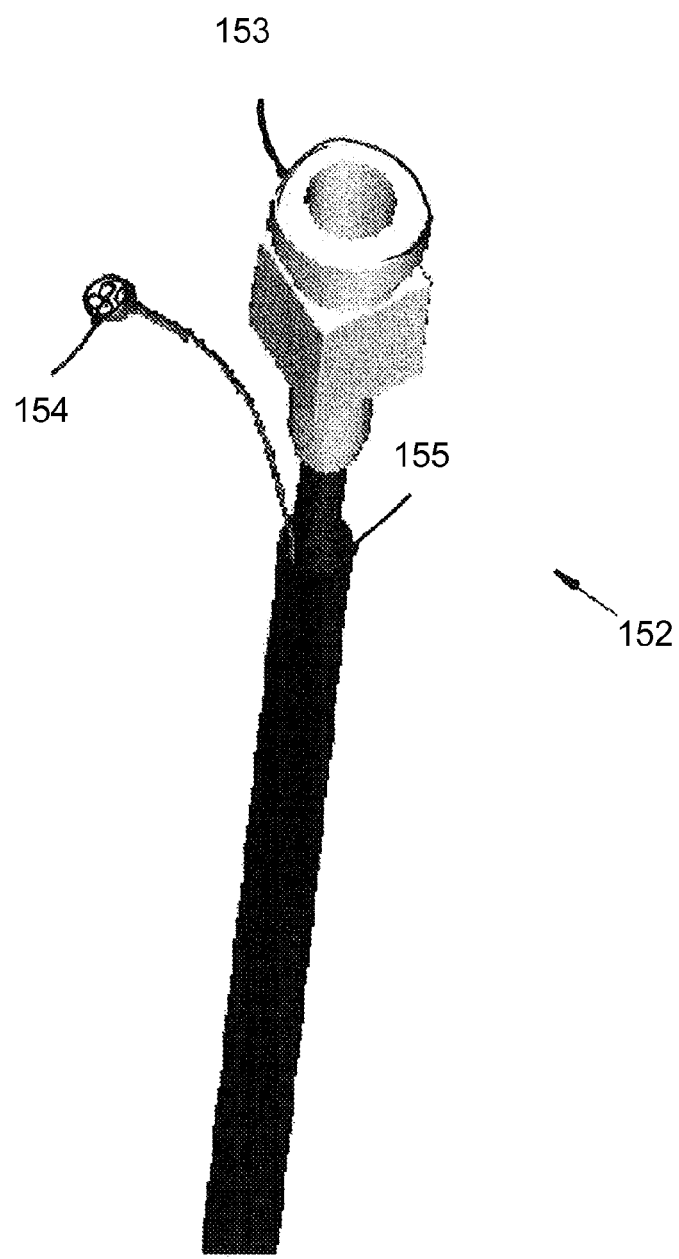
FIG. 9 schematically depicts the proximal end of a catheter according to FIG. 8.

FIG. 9 schematically depicts the proximal user interface (152) of the previously mentioned EV-CBIU in a selected embodiment of the present invention. A standard endovascular angiography port (153), an electrical connector (154) and an endovascular sheath (155)

Figure 10:
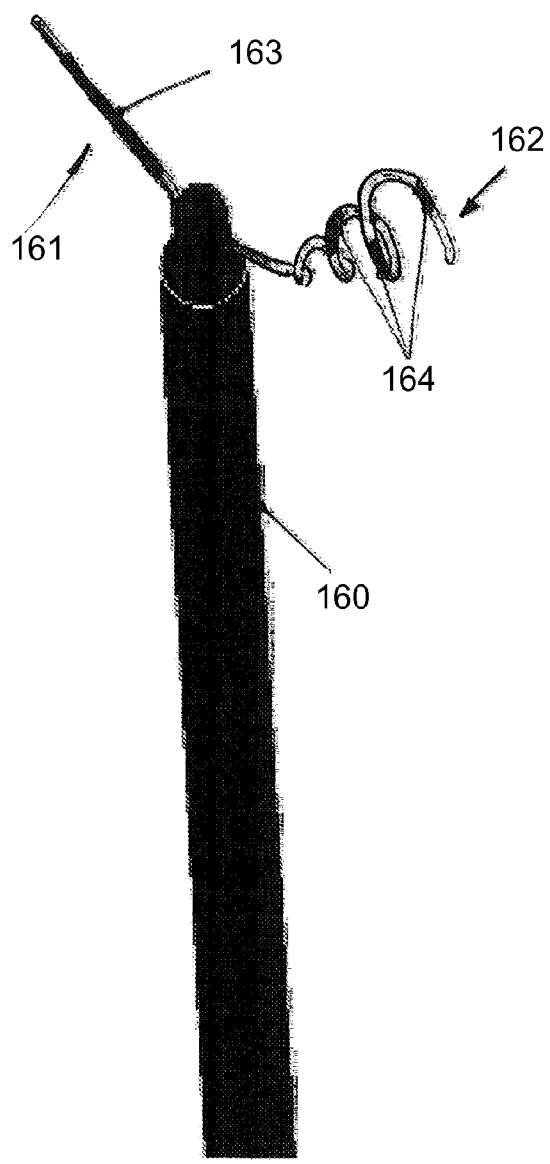
FIG. 10 schematically depicts the distal end of a catheter according to FIG. 8.

FIG. 10 schematically depicts the distal electrode end (DEE) of the previously mentioned EV-CBIU in a selected embodiment of the present invention. The DEE is shown to comprise a first stimulation electrode (161) and a second stimulation electrode (162). A generally cylindrical metal foil serves as the conductive surface member (163) in the first stimulation first stimulation electrode (161). Three generally cylindrical metal foils serve as the conductive surface members (164) in the second stimulation electrode (162). An endovascular sheath (160) is also shown.

Figure 11A:
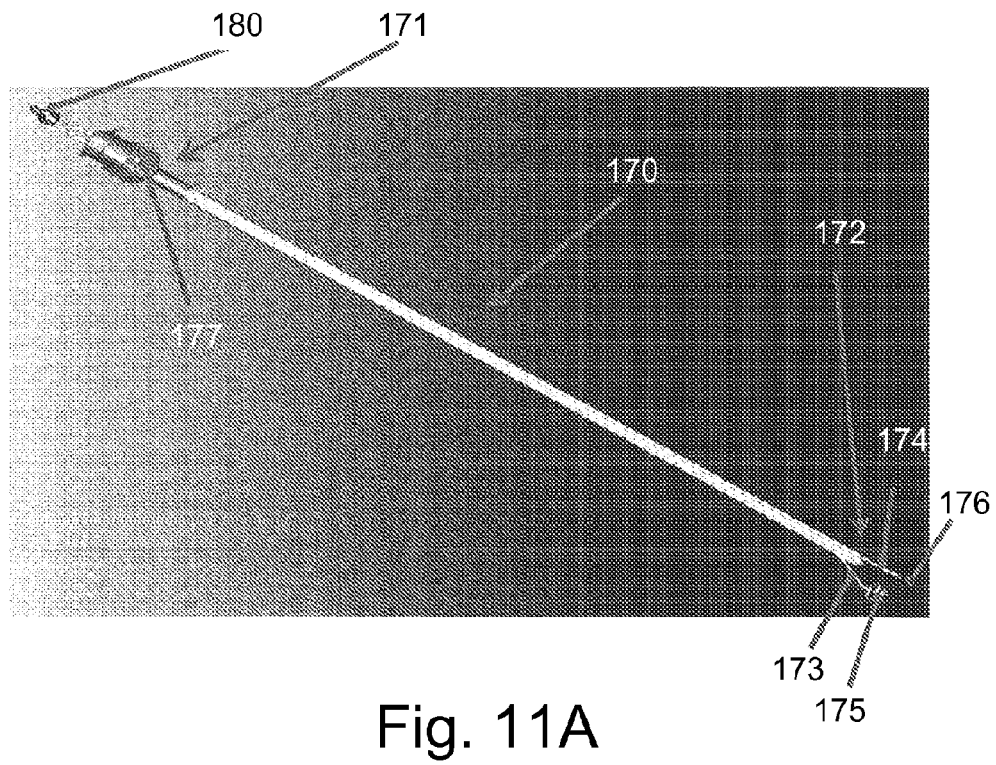
FIG. 11 schematically depicts an implantable electrostimulation module (FIG. 11A) and it distal end comprising an anchoring member (FIG. 11B).
Figure 11B:
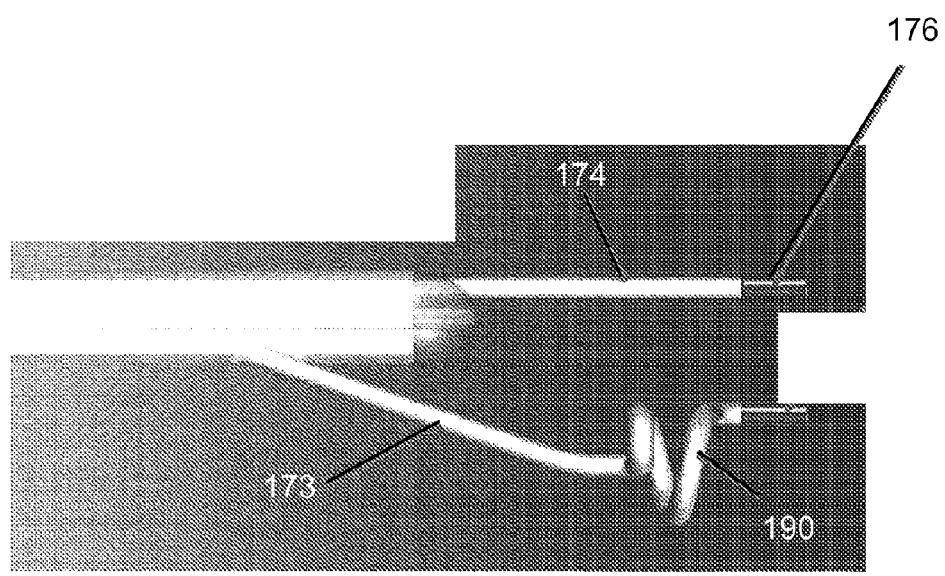

FIG. 11A schematically depicts an implantable electro-stimulation module comprising: (i) an elongated member (170) comprising a proximal (171) end and a multiple channel distal end (172), said multiple channel distal end (172) comprising a first (173) and a second (174) distal end members; (ii) a first metallic electrode (175) and a second metallic electrode (176) mounted to each of the said distal end members of the multiple channel distal end (172); (iii) two galvanically distinct wires (177) extending through said elongated member and connected to each of the said metallic electrode; and (iv) an electromagnetic transceiver (180) disposed at said proximal end of elongated member and connected to each of the galvanically distinct wires (177). FIG. 11B depicts the distal end of the elongated member, also showing in detail an endovascular anchoring member (190).

Figure 12:
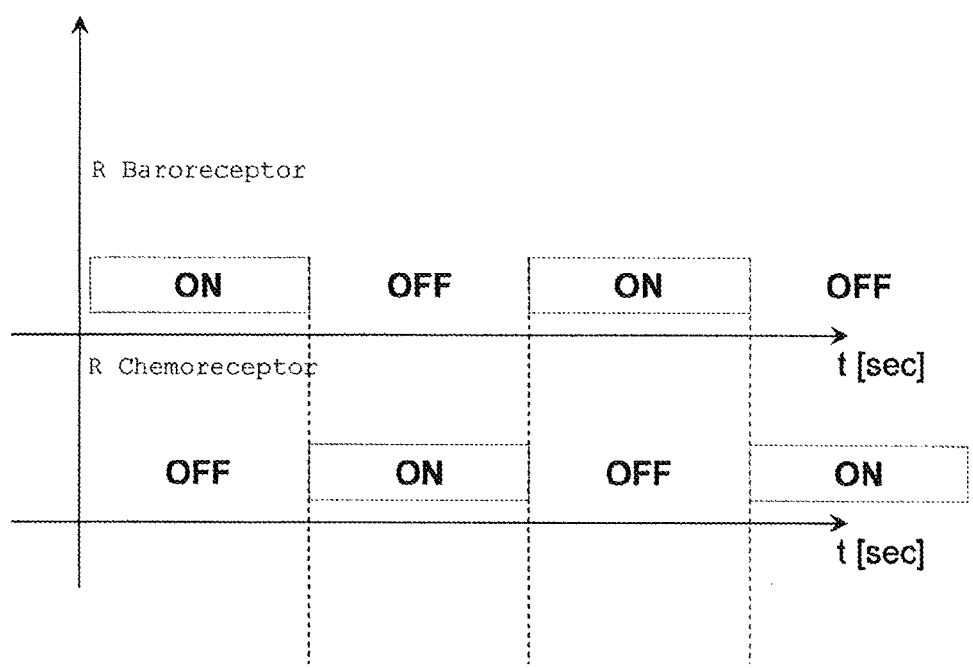
FIG. 12 to FIG. 16 depict intermittent stimulation regimens for the baroreceptors and chemoreceptors to be effected according to several embodiments of the system of the present invention.

FIG. 12 schematically depicts an intermittent unilateral stimulation regimen for the right baroreceptor and right chemoreceptor. In this selected embodiment of the present invention—either the right baroreceptor or the right chemoreceptor is activated. The two abovementioned receptors are not activated simultaneously.

Figure 13:
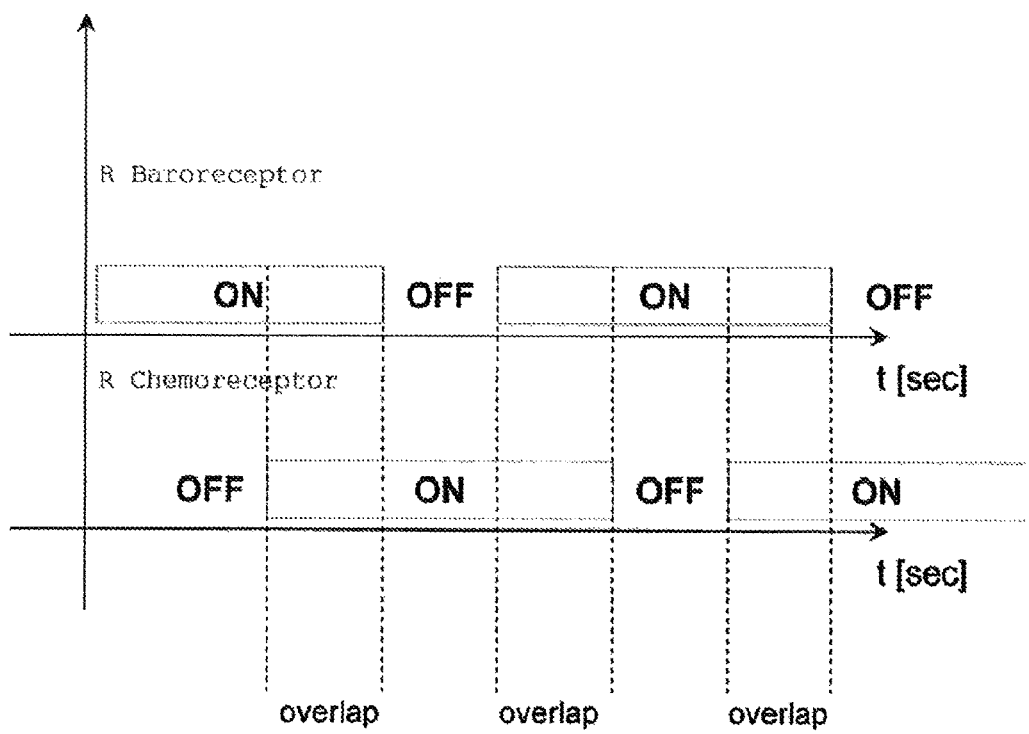

FIG. 13 schematically depicts an intermittent unilateral stimulation regimen for the right baroreceptor and right chemoreceptor. In this selected embodiment of the present invention—the right baroreceptor or the right chemoreceptor is activated—in a partially overlapping mode. Namely—there are times in which each of the receptors is activated alone, and times in which the two receptors are activated in tandem.

Figure 14:
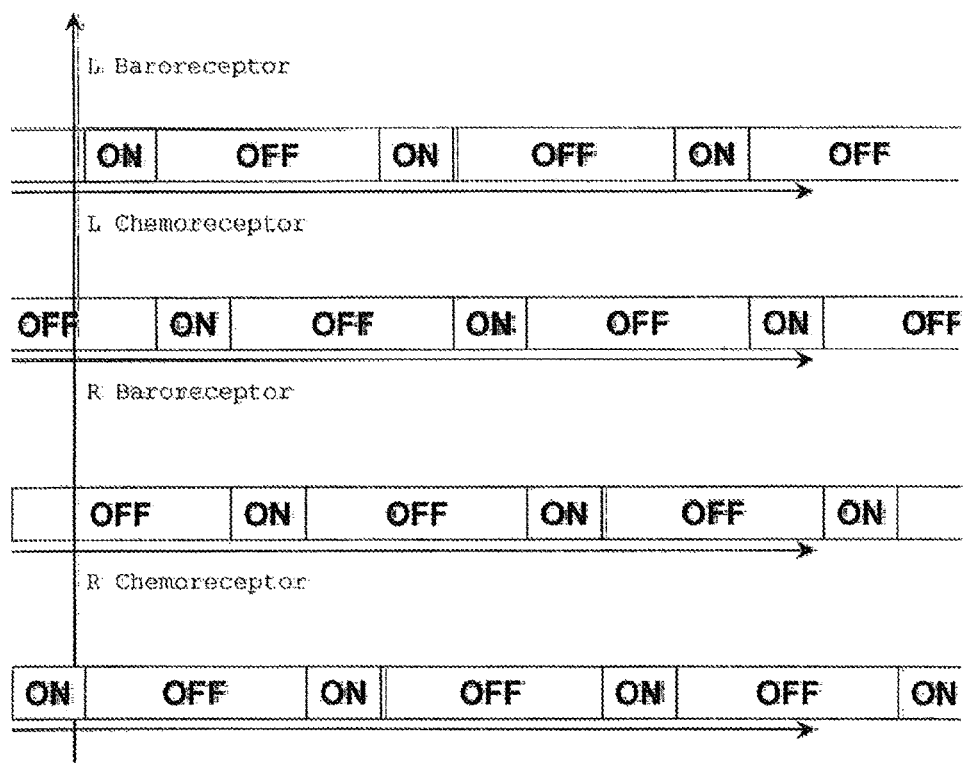

FIG. 14 schematically depicts an intermittent bilateral stimulation regimen for the right and left baroreceptors and for the right and left chemoreceptors. In this selected embodiment of the present invention—each of the four abovementioned receptors is activated alone—with the remaining three receptors left non-activated.

Figure 15:
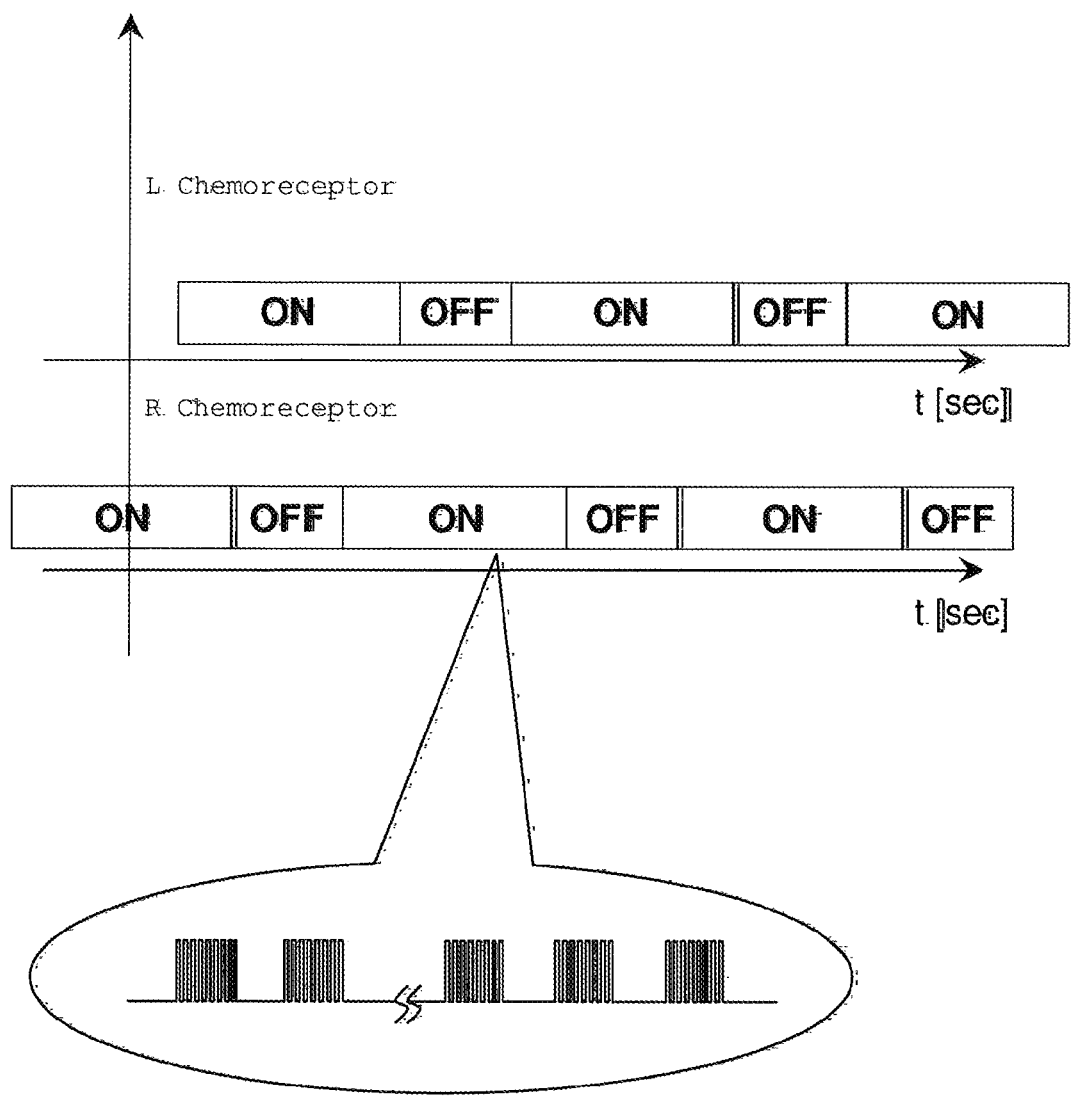

FIG. 15 schematically depicts an intermittent bilateral stimulation regimen for the right chemoreceptor and the left chemoreceptor. In this selected embodiment of the present invention—the right chemoreceptor or the left chemoreceptor is activated—in a partially overlapping mode. Namely—there are times in which each of the chemoreceptors is activated alone, and times in which the two chemoreceptors are activated in tandem. The balloon schematically depicts an example of an active stimulation period, which is comprised of a uniphasic pulse train, spaced by electrically-inactive periods that are intended to overcome neurological and biological tolerance to the stimulation regimen.

Figure 16:
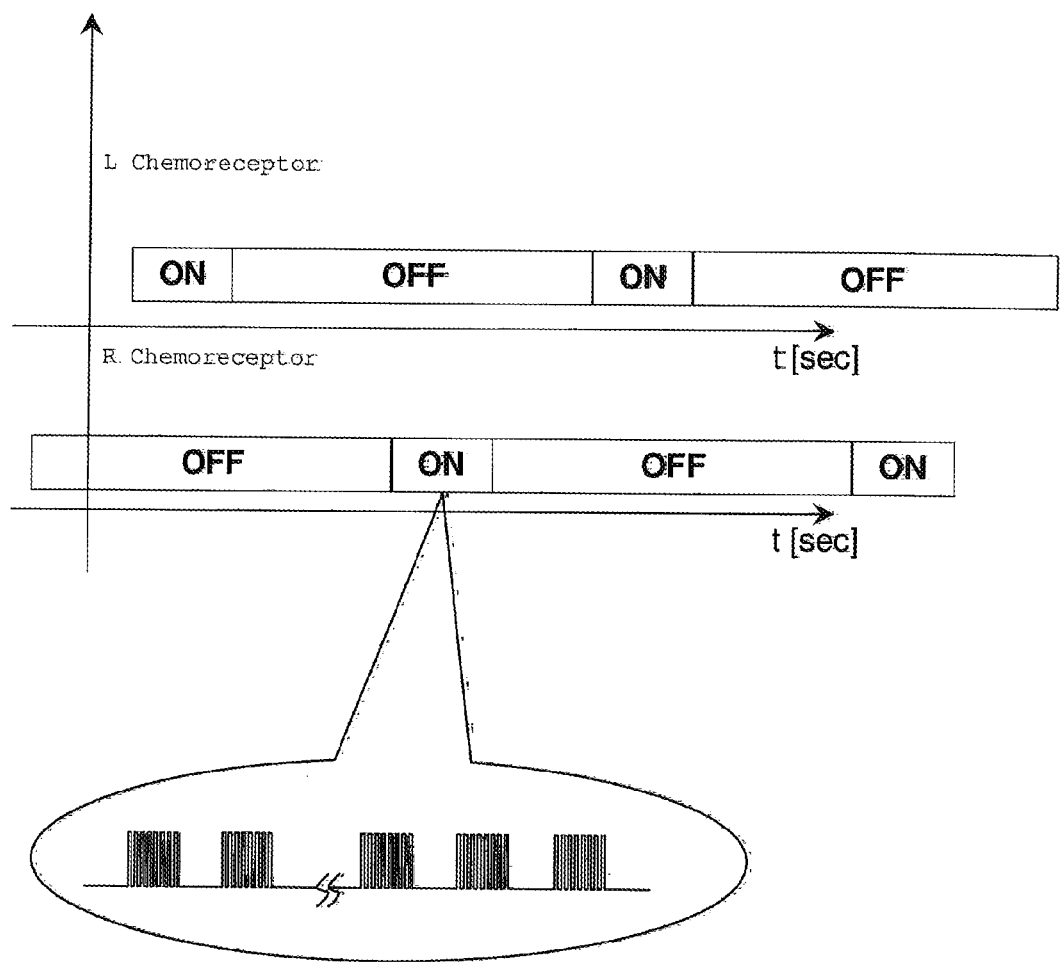

FIG. 16 schematically depicts an intermittent bilateral stimulation regimen for the right chemoreceptor and the left chemoreceptor. In this selected embodiment of the present invention—the right chemoreceptor or the left chemoreceptor is activated—in a non overlapping mode. Namely—there are times in which each of the chemoreceptors is activated alone, and times in none of the two chemoreceptors are activated.

The balloon schematically depicts an example of an active stimulation period, which is comprised of a uniphasic pulse train, spaced by electrically-inactive periods that are intended to overcome neurological and biological tolerance to the stimulation regimen.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

The invention claimed is:

1. A system for treating a cerebrovascular condition in a living body comprising:
   i) an implantable elongated electrostimulation module comprising a proximal end and a distal end, said distal end comprising a branching point at which said distal end is branched into at least a first and a second distal end member;
   (ii) at least one metallic electrode mounted to each of said first and second distal end members;
   (iii) an electromagnetic transceiver disposed at said proximal end;
   (iv) at least one conductive galvanically distinct wire extending through said module and connecting said transceiver with each of said electrodes; and
   (v) an electrical signal generator for producing an electrical waveform to be coupled to said electrodes; said module being sized and shaped for transient endovascular positioning near a carotid body of said living body, said branching point being adjacent to the bifurcation of said carotid, said at least first and second distal end members being adapted to be inserted into internal and external carotid arteries, thereby enabling the stimulation by said electrodes of chemoreceptors and optionally baroreceptors in said arteries adjacent to said bifurcation.

2. The system according to claim 1, wherein said module further comprises a generally tubular endovascular sheath, said sheath being disposed between said proximal end and said distal end, said sheath comprising one or more internal lumen, said lumen being adapted to house said conductive wire.

3. The system according to claim 1, further comprising means for estimating a cerebrovascular parameter selected from the group consisting of blood pressure, blood flow, blood velocity, and metabolic state of brain, said means being adjusted to generate a control signal indicative of said parameter, and wherein said electrical signal generator is capable of adapting said electrical waveform in accordance with said control signal so as to maintain a closed-loop control over said parameter.

4. The system according to claim 3, wherein said parameter is blood flow and comprises the duration and intensity of vasodilation, and wherein said control signal results in said electrical signal generator inducing a regimen of intermittently substantially normal and substantially increased blood flow, so as to prevent tolerance to said control signal.

5. The system according to claim 1, wherein said electrical waveform comprises a pulse train consisting of intermittently active and inactive periods, said active periods being characterized by a substantially non-zero electrical energy and said inactive period by zero electrical energy contained in said waveform.

6. The system according to claim 1, wherein said cerebrovascular condition is selected from the group consisting of cerebral hemorrhage, subarachnoid hemorrhage, cerebral vasospasm, brain ischemia, ischemic stroke, and traumatic brain injury.

7. The system according to claim 1, wherein said distal end member is flexible and has a shape selected from the group consisting of serpentine, spiral, and helical.

8. The system according to claim 1, wherein said system further comprises an endovascular anchoring member being capable of assuming (a) a collapsed state adapted to allow free longitudinal motion of said endovascular electrode inside a blood vessel lumen, and (b) a radially expanded state adapted to engage at least a longitudinal and an angular portion of said lumen, said endovascular anchoring member being reversibly transitioned between said collapsed state and radially expanded states.

* * * * *